United States Patent
Rauch

(10) Patent No.: US 9,333,046 B2
(45) Date of Patent: May 10, 2016

(54) SURGICAL INSTRUMENT TIP CLEANER

(71) Applicant: Steven Scott Rauch, Short Hills, NJ (US)

(72) Inventor: Steven Scott Rauch, Short Hills, NJ (US)

( * ) Notice: Subject to any disclaimer, the term of this patent is extended or adjusted under 35 U.S.C. 154(b) by 575 days.

(21) Appl. No.: 13/930,020

(22) Filed: Jun. 28, 2013

(65) Prior Publication Data
US 2014/0109328 A1    Apr. 24, 2014

Related U.S. Application Data

(60) Provisional application No. 61/717,002, filed on Oct. 22, 2012.

(51) Int. Cl.
| | | |
|---|---|---|
| *A47L 5/00* | (2006.01) | |
| *A61B 19/00* | (2006.01) | |
| *B08B 1/00* | (2006.01) | |
| *B08B 9/032* | (2006.01) | |
| *B08B 5/02* | (2006.01) | |
| *B08B 3/02* | (2006.01) | |
| *A47L 9/02* | (2006.01) | |
| *A47L 9/00* | (2006.01) | |

(52) U.S. Cl.
CPC . *A61B 19/34* (2013.01); *A47L 5/00* (2013.01); *A47L 9/0072* (2013.01); *A47L 9/02* (2013.01); *B08B 1/006* (2013.01); *B08B 3/026* (2013.01); *B08B 5/02* (2013.01); *B08B 9/032* (2013.01)

(58) Field of Classification Search
CPC ........... A47L 5/00; A47L 9/02; A47L 9/0072; B08B 1/006; B08B 3/026; B08B 5/02; B08B 9/032; B08B 9/035
USPC ................. 15/97.1, 209.1, 210.1, 218, 218.1, 15/220.4, 229.11, 229.13
IPC ......................................................... A47L 5/00
See application file for complete search history.

(56) References Cited

U.S. PATENT DOCUMENTS

| | | | |
|---|---|---|---|
| 4,543,751 A | 10/1985 | Alikhan | |
| 4,547,923 A * | 10/1985 | DeVries | A47L 21/04 15/104.001 |
| 4,704,760 A * | 11/1987 | Grieshaber | A61B 19/34 15/218.1 |
| 4,752,983 A * | 6/1988 | Grieshaber | B24D 15/04 15/160 |
| 5,016,401 A | 5/1991 | Mangus | |
| 5,392,766 A | 2/1995 | Masterson | |
| 5,514,084 A | 5/1996 | Fisher | |
| 5,778,480 A * | 7/1998 | Nittinger | A61C 19/00 15/210.1 |
| 6,006,391 A * | 12/1999 | Shurtliff | H01L 21/67028 15/102 |
| 6,021,540 A * | 2/2000 | Miller | A46B 9/06 15/160 |
| 6,725,492 B2 | 4/2004 | Moore | |
| 6,964,078 B2 * | 11/2005 | Schwab | B08B 1/00 15/218.1 |
| 7,780,794 B2 | 8/2010 | Rogers | |
| 8,001,645 B2 | 8/2011 | Kaufman | |

* cited by examiner

*Primary Examiner* — David Redding
(74) *Attorney, Agent, or Firm* — Marc D. Lowy

(57) ABSTRACT

The present invention is a tool for use during surgical procedures for cleaning tissue and debris from the in-vivo end of surgical instruments. The tool is used during various surgical procedures to clean debris from various surgical instruments. A substantially cylindrical, hollow shaft extends from one or both ends of the invention. An elastomeric suction tip coupler is configured at one or both ends of the hollow shaft to allow connection of commonly used suction tips. The invention includes a plurality of substantially parallel, elastomerized, concentric cleaning blades. The user of the invention may insert or swipe an instrument to be cleaned along cleaning blade edges configured at the peripheries of the cleaning blades, thereby causing the instrument to be cleaned. A hollow suction bulb, either integrated or stand-alone, is used to force fluid through clogged, commonly used suction tips in a backwash fashion, thereby clearing them of debris.

15 Claims, 4 Drawing Sheets

SURGICAL INSTRUMENT TIP CLEANER

CROSS REFERENCE TO RELATED APPLICATION(S)

This application claims the benefit of U.S. Provisional Application No. 61/717,002, filed Oct. 22, 2012, which is incorporated by reference as if fully set forth.

FIELD OF INVENTION

The present invention relates to a Surgical Instrument Tip Cleaner, and more particularly, to a tool for use in the surgical setting for cleaning tissue and debris from the in-vivo end of surgical instruments.

BACKGROUND

During surgical procedures, in-vivo instrument ends accumulate various types of debris that must be periodically cleaned. Current practice during surgical procedures is for medical personnel to use a gauze sponge to pinch, wipe and catch the debris from the in-vivo instrument ends. This cleaning process is usually performed many times during a surgical procedure as the surgeon mobilizes and exposes various pathologies in the surgical area.

The present invention is a tool used during various surgical procedures, including neuro-surgical and orthopedic surgical procedures, to clean debris from various surgical instruments. The surgical instruments may include, among others, bi-polar forceps, kerrison rongeur punches, pituitary rongeurs, other rongeurs, other instruments, and suction tips.

The invention will therefore reduce repetitive stress injuries for scrubbed medical personnel such as surgeons, surgical technologists, surgical scrub nurses, first assistants, and the like. The invention is expected to speed up the operative procedure by permitting the surgeon to clear the working instrument more easily, and in some instances by himself, merely by inserting the instrument into the concentric plate area, or else by drawing the instrument across the invention.

The invention also quickens the cleaning of clogged suction tips since the bulb syringes commonly provided do not connect or couple to the commonly provided suction tips, thus requiring the scrub person to use a 20 mL or other size leur locking, or non-leur locking syringe for this cleaning purpose.

Clearly there is a need for an effective tool to clean the debris from in-vivo instrument ends during surgical procedures. The present invention accomplishes this objective.

SUMMARY

The present invention is a hand held tool for use during surgical procedures for cleaning tissue and debris from the in-vivo end of surgical instruments. The tool is used during neuro-surgical and orthopedic surgical procedures to clean debris from various surgical instruments. The surgical instruments may include, among others, bi-polar forceps, kerrison rongeur punches, pituitary rongeurs, other rongeurs, other instruments, and suction tips.

In one embodiment of the invention, a substantially cylindrical hollow shaft extends from the proximal end of the invention. An elastomeric suction tip coupler is configured at the end of the hollow shaft to allow direct connection of commonly used suction tips.

The hollow shaft connects to and extends within a cleaning assembly comprised of a plurality of adjacent, substantially parallel, elastomerized, concentric cleaning blades. The user of the invention cleans a surgical instrument by inserting or swiping the surgical instrument along non-abrasive, high friction instrument cleaning blade edges configured at the peripheries of the cleaning blades, thereby causing the transfer of surgical debris from the instrument to be cleaned to the invention. The cleaning blades may be configured in various geometric shapes including round, square, and hexagonal shapes. Spaces between the cleaning blades are configured to allow access to the cleaning blade edges. The cleaning blade edges include various end and edge configurations such as rounded, square, bulbous, knife edge, tee shaped, and the like.

In one embodiment of the invention, the distal end of the hollow shaft extending within the cleaning assembly connects to an integrated hollow suction bulb configured to draw up and hold irrigation fluid provided for the surgical procedure. Commonly used suction tips including frazier, brachman, rhoton, yankaur and other types may be connected to the suction tip coupler at the proximal end of the hollow shaft. Using either the integrated suction bulb, or (in other embodiments) a stand-alone bulb syringe, the user can force fluid through clogged suction tips in a backwash fashion, thereby clearing them and cleaning them of debris.

The invention can be sterilized for use within the sterile field and can be either re-used or else can be disposable. The invention size and weight may be configured in various embodiments, including hand-held embodiments, an embodiment with the invention attached to the patient drape, and an embodiment with the invention configured for mounting on the edge of overhanging furniture, ie mayo stand.

Some embodiments of the invention include a stand-alone bulb syringe. In these embodiments, a substantially cylindrical hollow shaft extends from both ends of the invention. An elastomeric suction tip coupler is configured at the proximal end of the hollow shaft to allow direct connection of commonly used suction tips. After connecting a suction tip to one suction tip coupler, the invention user can then connect the tip of the stand-alone bulb syringe to the remaining end of the hollow shaft, and force fluid through the clogged suction tip in a backwash fashion, thereby clearing it of debris.

One embodiment of the surgical instrument tip cleaner includes a flexible, substantially flat base that can be clipped or secured with a hemostat, or other clamp, to the patient drapes in the operative field. The flat base is strong enough to prevent instruments from accidentally penetrating the flat base and thus possibly injuring the patient. A plurality of holes are configured in the flat base as a reminder for medical personnel to use a hemostat clamp or other clamp to secure the flat base to surgical drapes. Other embodiments of the invention might include double sided tape to attach the flat base to surgical drapes.

Another embodiment of the invention includes an attachment base configured to attach the invention, by clamping action or other means, to a mayo stand, or other table edge over the operative field. The attachment base is configured to adapt to a range of table or stand edge thicknesses.

Other features and advantages of the present invention will become apparent from the following more detailed description, taken in conjunction with the accompanying drawings, which illustrate, by way of example, the principles of the invention.

BRIEF DESCRIPTION OF THE DRAWING(S)

The foregoing Summary as well as the following detailed description will be readily understood in conjunction with the appended drawings which illustrate embodiments of the invention. In the drawings.

DETAILED DESCRIPTION OF ILLUSTRATIVE EMBODIMENT(S)

The present invention 10 is a hand held tool for use during surgical procedures for cleaning tissue and debris from the in-vivo end of surgical instruments. The tool 10 is used during neuro-surgical and orthopedic surgical procedures to clean debris from various surgical instruments. The surgical instruments may include, among others, bi-polar forceps, kerrison rongeur punches, pituitary rongeurs, other rongeurs, other instruments, and suction tips.

Figure 1:
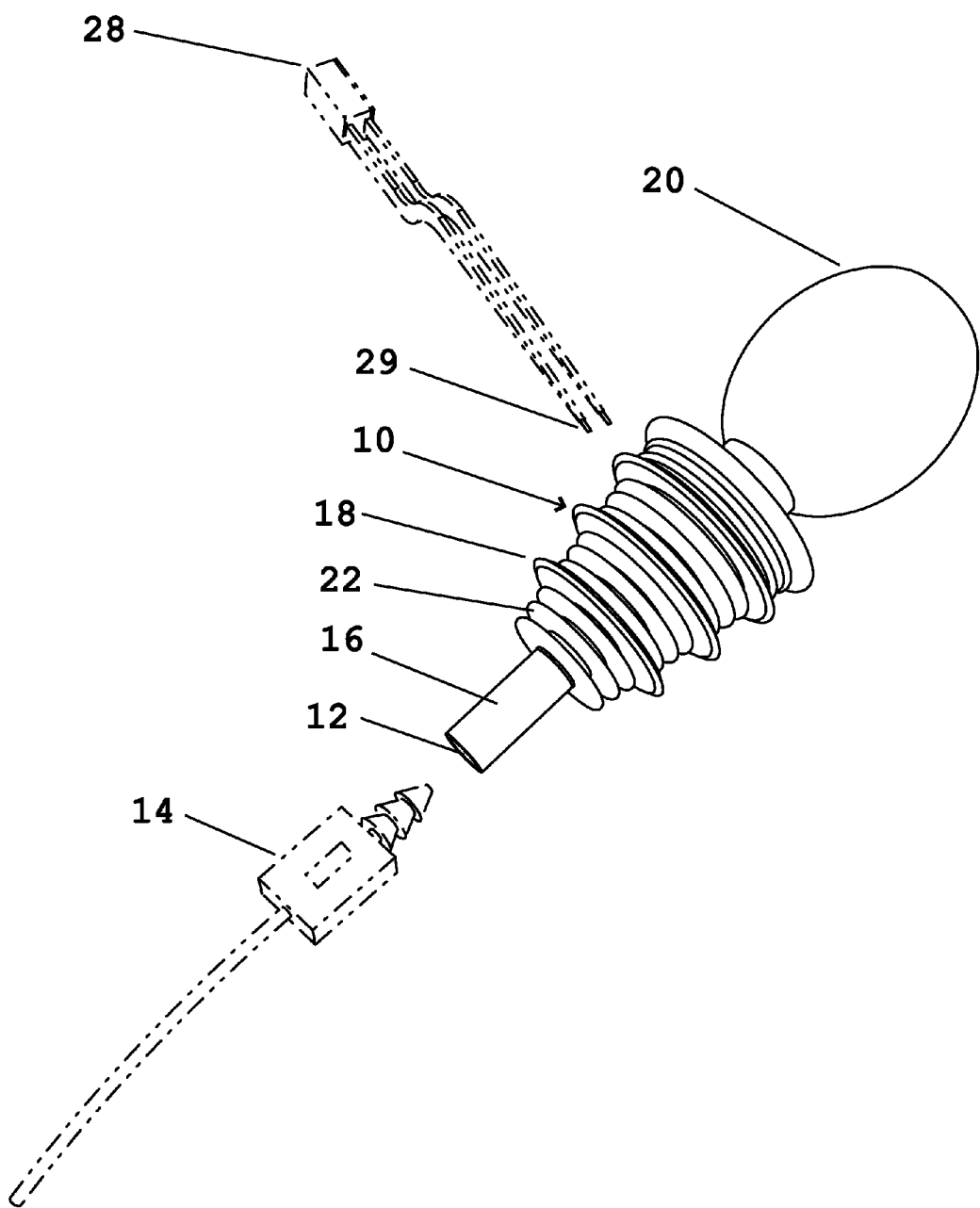
FIG. 1 illustrates an embodiment of a Surgical Instrument Tip Cleaner with an Integral Bulb Syringe.

Referring to FIG. 1, an embodiment of a hand held surgical instrument tip cleaner 10 with an integral bulb syringe 20 is illustrated. A substantially cylindrical, hollow shaft 16 extends within the invention 10, and extends from the proximal end of the invention 10. An elastomeric suction tip coupler 12 is configured at the proximal end of the hollow shaft 16 to allow direct connection of commonly used suction tips 14.

The hollow shaft 16 connects to and extends within a plurality of adjacent, substantially parallel, elastomerized, concentric cleaning blades 22. Non-abrasive, high friction instrument cleaning blade edges 18 are configured at the peripheries of the cleaning blades 22. In some embodiments of the invention 10, all or some of the cleaning blade edges 18 may be configured with gaps or discontinuities. At multiple locations along and between the various cleaning blades 22, the user of the invention 10 may insert the open tips 29 of an instrument 28 to be cleaned, so that one or more cleaning blades 22 extend between the tips 29. The user then withdraws the instrument 28 while exerting a pinching pressure on the tips 29 sufficient to cause friction. This action thereby cleans the inside portion of the tips 29 by causing the transfer of surgical debris from the tips 29 of the instrument 28 to the invention 10.

The cleaning blades 22 may be configured in various geometric shapes including round, square, and hexagonal shapes. Spaces between the cleaning blades 22 are configured so that the cleaning blades 22 provide multiple, non-abrasive high friction instrument cleaning surfaces. The cleaning blades 22 include various cleaning blade edge 18 configurations such as rounded, square, bulbous, knife edge, tee shaped, and the like. The surfaces of the cleaning blades 22 may also be configured with varied textures, including non-abrasive textures, high friction textures, with and without perforations, with and without ridges and dimples.

The hollow shaft distal end 36 connects to an integrated hollow suction bulb 20 configured to draw up and hold irrigation fluid provided for the surgical procedure. Commonly used suction tips 14 including frazier, brachman, rhoton, yankaur and other types may be connected to the proximal suction tip coupler 12. Using either the integrated suction bulb 20, or else a stand-alone bulb syringe 32 (FIG. 2), the user can force fluid through clogged suction tips 14 in a backwash fashion, thereby clearing them and cleaning them of debris.

The invention 10 can be sterilized for use within the sterile field and can be either re-used or else can be disposable. The invention 10 size and weight may be configured in various embodiments, including hand-held embodiments (FIGS. 1-2), an embodiment with the invention 10 attached to a patient drape (FIG. 3), and an embodiment with the invention 10 configured for mounting on the edge of overhanging furniture, such as a mayo stand (FIG. 4).

Figure 2:
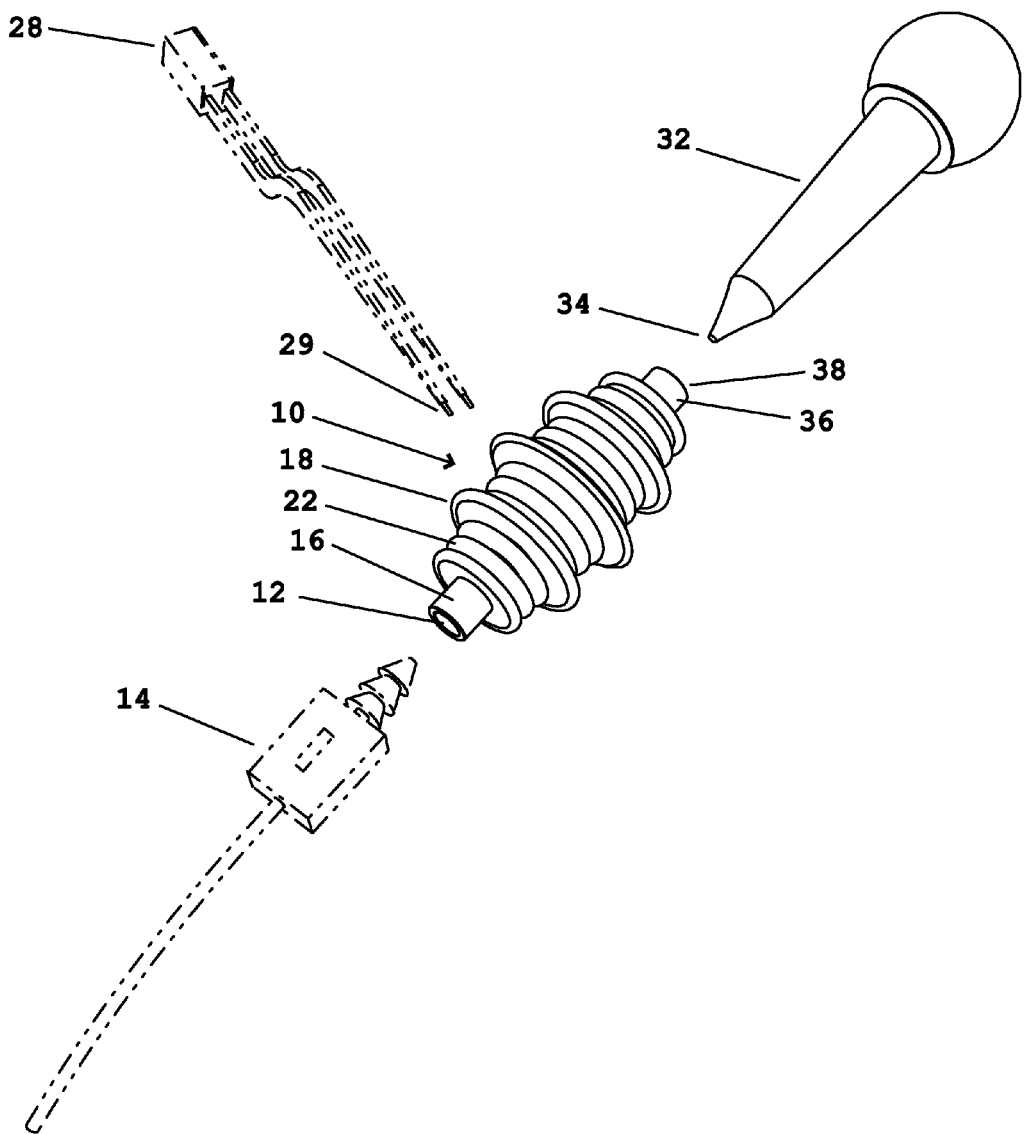
FIG. 2 illustrates an embodiment of a Surgical Instrument Tip Cleaner with a Stand-Alone Bulb Syringe.

Referring to FIG. 2, an embodiment of a hand held surgical instrument tip cleaner 10 with a stand-alone bulb syringe 32 is illustrated. In this embodiment of the invention 10, substantially cylindrical, a hollow shaft 16 extends within the invention 10 and extends from both sides of the invention 10. The stand-alone bulb syringe 32 is configured for cleaning a suction tip 14. Elastomeric proximal and distal suction tip couplers 12, 38 are configured at the ends of the hollow shaft 16 to allow direct connection of commonly used suction tips 14. After connecting a suction tip 14 to a suction tip coupler 12 the invention 10 user can then connect the tip 34 of the stand-alone bulb syringe 32 to the opposite end of the hollow shaft 16 and force fluid through the clogged suction tip 14 in a backwash fashion, thereby clearing it of debris.

The hollow shaft 16 connects to and extends within a plurality of substantially parallel, adjacent, elastomerized, concentric cleaning blades 22. Non-abrasive, high friction instrument cleaning blade edges 18 are configured at the peripheries of the cleaning blades 22. All or some of the cleaning blade edges 18 may be configured with gaps or discontinuities. At multiple locations along and between the various cleaning blades 22, the user of the invention 10 may insert the open tips 29 of an instrument 28 to be cleaned, so that one or more cleaning blades 22 extend between the tips 29. The user then withdraws the instrument 28 while exerting a pinching pressure on the tips 29 sufficient to cause friction. This action thereby cleans the inside portion of the tips 29 by causing the transfer of surgical debris from the tips 29 of the instrument 28 to the invention 10.

The cleaning blades 22 may be configured in various geometric shapes including round, square, and hexagonal shapes. Spaces between the cleaning blades 22 are configured so that the cleaning blades 22 provide multiple, non-abrasive high friction instrument cleaning surfaces. The cleaning blades 22 include various cleaning blade edge 18 configurations such as rounded, square, bulbous, knife edge, tee shaped, and the like. The surfaces of the cleaning blades 22 may also be configured with varied textures, including non-abrasive textures, high friction textures, with and without perforations, with and without ridges and dimples.

Figure 3:
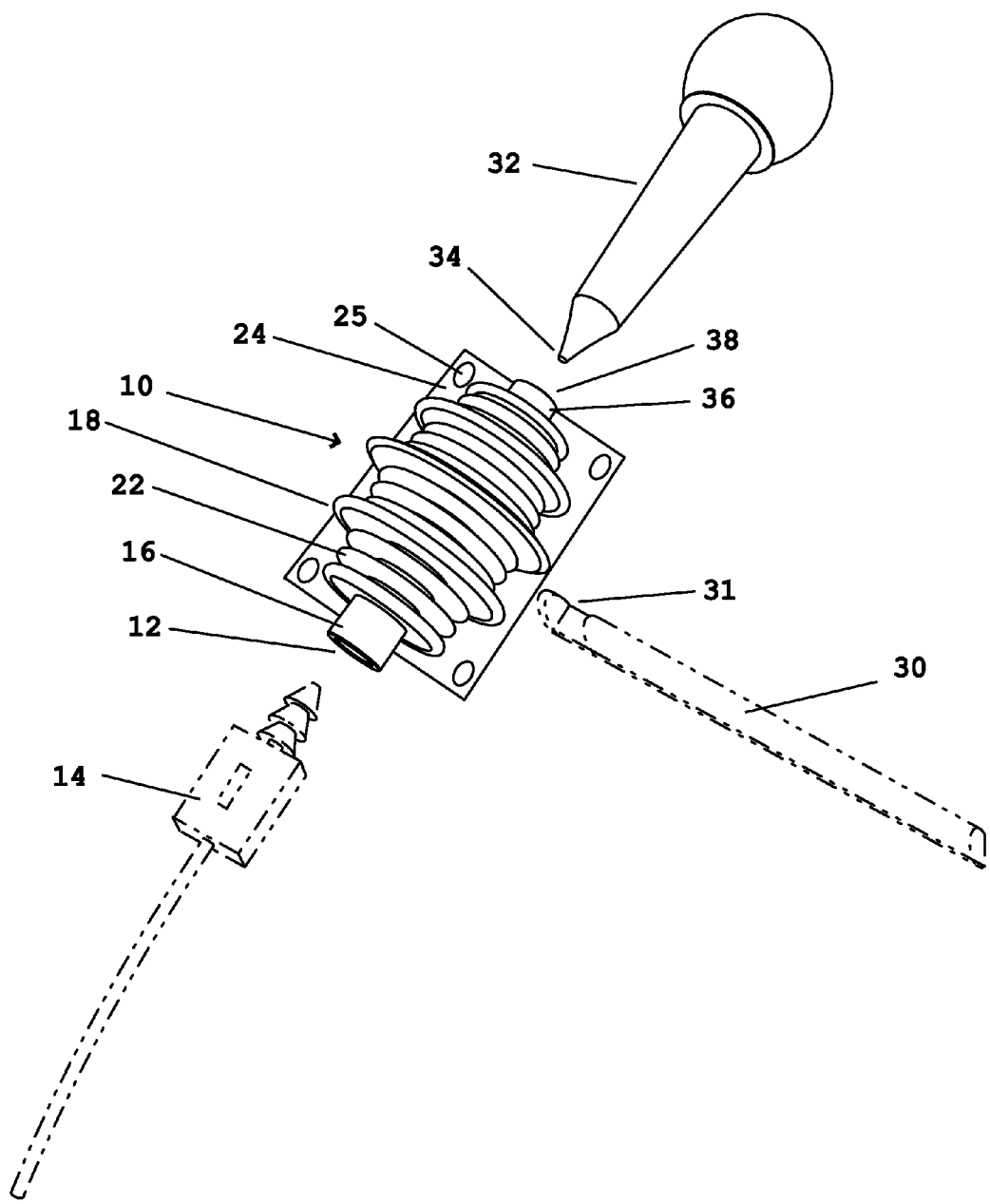
FIG. 3 illustrates an embodiment of a Surgical Instrument Tip Cleaner with a Stand-Alone Bulb Syringe and a Flat Base.
Figure 4:
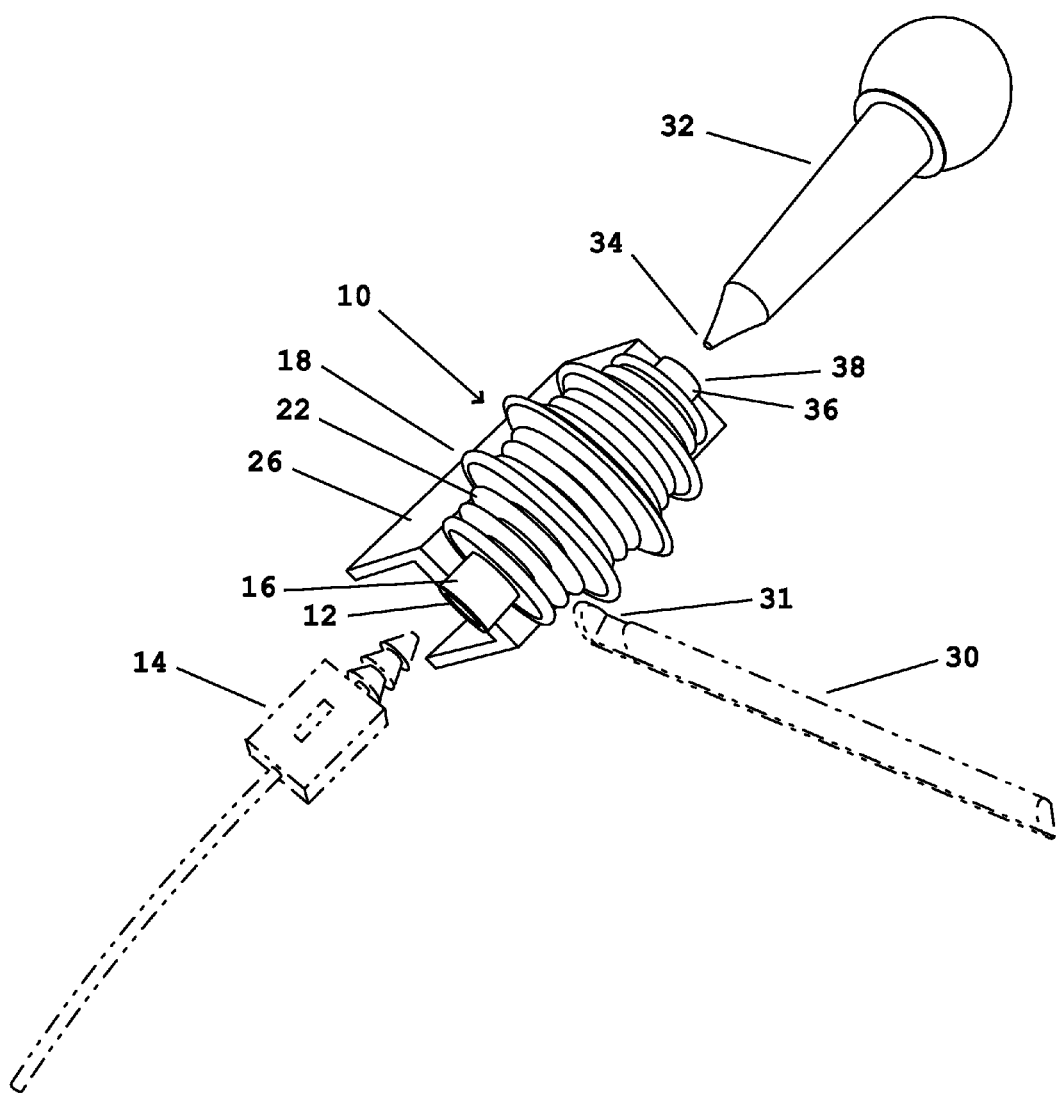
FIG. 4 illustrates an embodiment of a Surgical Instrument Tip Cleaner with a Stand-Alone Bulb Syringe and an Attachment Base.

Referring to FIG. 3, an embodiment of the surgical instrument tip cleaner 10 with a flat base 24 for attachment to patient drapes, along with a stand-alone bulb syringe 32 is illustrated. This embodiment of the invention 10 includes a flexible, substantially flat base 24 that can be clipped or secured with a hemostat, or other clamp, to the patient drapes in the operative field. The flat base 24 is strong enough to prevent instruments from accidentally penetrating the flat base 24 and thus possibly injuring the patient. A plurality of holes 25 are configured in the flat base 24 as a reminder for medical personnel to use a hemostat clamp or other clamp to secure the flat base 24 to surgical drapes. Other embodiments of the invention might include double sided tape to attach the flat base 24 to surgical drapes.

In this embodiment of the invention 10, a substantially cylindrical, hollow shaft 16 extends within the invention 10 and extends from both sides of the invention 10. The hollow shaft 16 connects to and extends within a plurality of substantially parallel, adjacent, elastomerized, concentric cleaning blades 22.

The cleaning blades 22 may be configured in various geometric shapes including round, square, and hexagonal shapes. Spaces between the cleaning blades 22 are configured so that the cleaning blades 22 provide multiple, non-abrasive high friction instrument cleaning surfaces. The cleaning blades 22 include various cleaning blade edge 18 configurations such as rounded, square, bulbous, knife edge, tee shaped, and the like. The surfaces of the cleaning blades 22 may also be configured with varied textures, including non-abrasive textures, high friction textures, with and without perforations, with and without ridges and dimples.

In some embodiments of the invention 10, all or some of the cleaning blade edges 18 may be configured with gaps or discontinuities. At multiple locations along and between the various cleaning blades 22, the user of the invention 10 may first insert the tip 31 of an instrument 30 to be cleaned, then twist, wipe, or rub, and then withdraw the tip 31 of the instrument 30, thereby causing the transfer of surgical debris from the tip 31 of the instrument 30 to the invention 10.

A stand-alone, fluid filled bulb syringe 32 is configured for cleaning a suction tip 14. Elastomeric suction tip couplers 12,38 are configured at the ends of the hollow shaft 16 to allow direct connection of commonly used suction tips 14, and connection of the tip 34 of the stand-alone, fluid filled bulb syringe 32 to the hollow shaft 16. The invention 10 user can then force fluid through the clogged suction tip 14 in a backwash fashion, thereby clearing and cleaning it of debris.

Referring to FIG. 4, an embodiment of a Surgical Instrument Tip Cleaner 10, including a stand-alone bulb syringe 32 is illustrated. This embodiment of the invention 10 includes an attachment base 26 configured to attach the invention 10, by clamping action or other means, to a mayo stand, or other table edge over the operative field. The attachment base 26 is configured to adapt to a range of table or stand edge thicknesses. The orientation of the invention 10 shown in FIG. 4 may be at different angles than horizontal.

In this embodiment of the invention 10, a substantially cylindrical, hollow shaft 16 extends within the invention 10, and extends from both sides of the invention 10. The hollow shaft 16 connects to and extends within a plurality of substantially parallel, adjacent, elastomerized, concentric cleaning blades 22.

The cleaning blades 22 may be configured in various geometric shapes including round, square, and hexagonal shapes. Spaces between the cleaning blades 22 are configured so that the cleaning blades 22 provide multiple, non-abrasive high friction instrument cleaning surfaces. The cleaning blades 22 include various cleaning blade edge 18 configurations such as rounded, square, bulbous, knife edge, tee shaped, and the like. The surfaces of the cleaning blades 22 may also be configured with varied textures, including non-abrasive textures, high friction textures, with and without perforations, with and without ridges and dimples.

In some embodiments of the invention 10, all or some of the cleaning blade edges 18 may be configured with gaps or discontinuities. At multiple locations along and between the various cleaning blades 22, the user of the invention 10 may first insert the tip 31 of an instrument 30 to be cleaned, then twist, wipe, or rub, and then withdraw the tip 31 of the instrument 30, thereby causing the transfer of surgical debris from the tip 31 of the instrument 30 to the invention 10.

A stand-alone, fluid filled bulb syringe 32 is configured for cleaning a suction tip 14. Elastomeric suction tip couplers 12,38 are configured at the ends of the hollow shaft 16 to allow direct connection of commonly used suction tips 14 to the hollow shaft 16, and connection of the stand-alone, fluid filled bulb syringe 32 to the opposite end of hollow shaft 16.

The invention 10 may be utilized within the sterile surgical field, to be either hand-held by one of the scrubbed personnel (FIGS. 1-2), or else attached to the patient drapes (FIG. 3), or else mounted to a surgical room fixture, such as a mayo stand, or head holder assembly (FIG. 4).

Using either the integrated suction bulb 20 (FIG. 1), or else a stand-alone bulb syringe 32 (FIGS. 2-4), the user can force fluid through clogged suction tips 14 in a backwash fashion, thereby clearing them of debris and cleaning them. Commonly used suction tips, including frazier, brachman, rhoton, yankaur and other types may be cleared with the invention 10. To clear a clogged suction tip 14, the invention 10 user attaches the clogged suction tip 14 to one of the suction tip couplers 12, 38. If the standalone bulb 32 embodiment of the invention 10 is being used, the user then connects the stand-alone bulb syringe 32 to the remaining suction tip coupler 12, 38 (FIGS. 2-4). The user then compresses either the integrated suction bulb 20, or else the stand-alone suction bulb 32 to force the retained fluid through the hollow shafts 16,36 to the suction tip 14 under pressure, thereby forcing the fluid and debris out of the suction tip 14 and cleaning and clearing the inside of the suction tip 14 from debris.

While embodiments of the invention have been described in detail above, the invention is not limited to the specific embodiments described above, which should be considered as merely exemplary illustrations set forth for a clear understanding of the principles of the invention. Further variations, modifications, extensions, or equivalents of the invention may be developed without departing from the scope of the invention. It is therefore intended that the invention not be limited to the particular embodiments disclosed as the best mode contemplated for carrying out this invention, but that the invention will include all the embodiments falling within the scope of the appended claims.

What is claimed is:

1. A tool for cleaning surgical instrument tips, comprising:
   a plurality of adjacent, substantially parallel, concentric cleaning blades,
   a substantially hollow shaft extending through said cleaning blades,
   a coupling mechanism configured at the proximal end of said hollow shaft,
   a flexible suction bulb configured at the distal end of said hollow shaft,
   whereby said tool will clear debris from various surgical instrument tips.

2. The tool for cleaning surgical instrument tips of claim 1, wherein said coupling mechanism comprises a suction tip coupler.

3. The tool for cleaning surgical instrument tips of claim 1, further including cleaning blade edges configured at the peripheries of said cleaning blades.

4. The tool for cleaning surgical instrument tips of claim 1, wherein the shape of said cleaning blades are selected from the group consisting of rounded, square, bulbous, knife edge, and tee shaped.

5. The tool for cleaning surgical instrument tips of claim 1, wherein the surface textures of said cleaning blades are selected from the group consisting of non-abrasive textures, high friction textures, perforated textures, non-perforated textures, ridge textures, and dimple textures.

6. A tool for cleaning surgical instrument tips, comprising:
   a plurality of adjacent, substantially parallel, concentric cleaning blades, a substantially hollow shaft extending through said cleaning blades, coupling mechanisms configured at the ends of said hollow shaft, a substantially flat base configured for mounting said tool, a standalone flexible suction bulb, whereby said tool will clear debris from various surgical instrument tips.

7. The tool for cleaning surgical instrument tips of claim 6, wherein said coupling mechanisms comprise suction tip couplers.

8. The tool for cleaning surgical instrument tips of claim 6, further including cleaning blade edges configured at the peripheries of said cleaning blades.

9. The tool for cleaning surgical instrument tips of claim 6, wherein the shape of said cleaning blades are selected from the group consisting of rounded, square, bulbous, knife edge, and tee shaped.

10. The tool for cleaning surgical instrument tips of claim 6, wherein the surface textures of said cleaning blades are selected from the group consisting of non-abrasive textures, high friction textures, perforated textures, non-perforated textures, ridge textures, and dimple textures.

11. A tool for cleaning surgical instrument tips, comprising:

a plurality of adjacent, substantially parallel, concentric cleaning blades, a substantially hollow shaft extending through said cleaning blades, coupling mechanisms configured at the ends of said hollow shaft, an attachment frame configured to attach said tool to a surgical room fixture, a standalone flexible suction bulb, whereby said tool will clear debris from various surgical instrument tips.

12. The tool for cleaning surgical instrument tips of claim 11, wherein said coupling mechanisms comprise suction tip couplers.

13. The tool for cleaning surgical instrument tips of claim 11, further including cleaning blade edges configured at the peripheries of said cleaning blades.

14. The tool for cleaning surgical instrument tips of claim 11, wherein the shape of said cleaning blades are selected from the group consisting of rounded, square, bulbous, knife edge, and tee shaped.

15. The tool for cleaning surgical instrument tips of claim 11, wherein the surface textures of said cleaning blades are selected from the group consisting of non-abrasive textures, high friction textures, perforated textures, non-perforated textures, ridge textures, and dimple textures.

\* \* \* \* \*